United States Patent
Wirtz et al.

(10) Patent No.: US 11,724,212 B2
(45) Date of Patent: Aug. 15, 2023

(54) ALCOHOL DEHYDRATION APPARATUS AND METHOD

(71) Applicant: MACH Technologies, Detroit, MI (US)

(72) Inventors: Robert N. Wirtz, Royal Oak, MI (US); Jason T. Wirtz, Royal Oak, MI (US); John W. Wirtz, II, Fort Gratiot, MI (US)

(73) Assignee: MACH Technologies, Detroit, MI (US)

( * ) Notice: Subject to any disclaimer, the term of this patent is extended or adjusted under 35 U.S.C. 154(b) by 196 days.

(21) Appl. No.: 17/225,195

(22) Filed: Apr. 8, 2021

(65) Prior Publication Data

US 2021/0339163 A1    Nov. 4, 2021

Related U.S. Application Data

(60) Provisional application No. 63/017,782, filed on Apr. 30, 2020.

(51) Int. Cl.
| | | |
|---|---|---|
| *C07C 29/76* | (2006.01) | |
| *C07C 31/08* | (2006.01) | |
| *B01D 5/00* | (2006.01) | |
| *B01D 61/36* | (2006.01) | |
| *B01D 1/22* | (2006.01) | |

(52) U.S. Cl.
CPC ............. *B01D 5/006* (2013.01); *B01D 1/221* (2013.01); *B01D 61/362* (2013.01); *C07C 29/76* (2013.01); *C07C 31/08* (2013.01)

(58) Field of Classification Search
CPC ......... C07C 29/76; C07C 31/08; B01D 5/006; B01D 61/362
See application file for complete search history.

(56) References Cited

U.S. PATENT DOCUMENTS

| | | |
|---|---|---|
| 5,498,339 A | 3/1996 | Creusen et al. |
| 2009/0269834 A1 | 10/2009 | Quinn |
| 2010/0240524 A1 | 9/2010 | Hilaly et al. |
| 2011/0229950 A1 | 9/2011 | Sovereign et al. |
| 2013/0206576 A1 | 8/2013 | Goel et al. |

OTHER PUBLICATIONS

International Preliminary Report on Patentability for International Application No. PCT/US2021/026321 dated Oct. 27, 2022 (11 pages).
Huang, et al. "Ethanol dehydration using hydrophobic and hydrophilic polymer membranes." Industrial & engineering chemical research 49.23 (Dec. 1, 2010): 12067-12070 col. 2 para 2; Figure 1; Figure 4; Figure 6 Figure 7. (7 pages).
International Search Report and Written Opinion for International Application No. PCT/US21/26321 dated Sep. 9, 2021 (27 pages).

*Primary Examiner* — Sikarl A Witherspoon
(74) *Attorney, Agent, or Firm* — Reising Ethington P.C.

(57) ABSTRACT

A process of and apparatus for dehydrating an alcohol/water mixture may include pressurizing the mixture to at least 40 psig, heating the pressurized mixture to a temperature of at least 170° F., passing the heated and pressurized mixture through at least one Zeolite separator to produce separate streams of water and pressurized and heated dehydrated alcohol, and using the pressurized and heated dehydrated alcohol to at least in part heat pressurized mixture and to cool the pressurized and heated dehydrated alcohol. At least some implementations may include cooling the pressurized and heated dehydrated alcohol to a temperature below its boiling point at atmospheric pressure. At least some implementations may include applying a vacuum to the water stream side of the Zeolite separator. At least some implementations may include cooling the stream of water to a temperature of less than about 200° F.

19 Claims, 3 Drawing Sheets

ALCOHOL DEHYDRATION APPARATUS AND METHOD

PRIORITY CLAIM

This patent application claims the priority of U.S. provisional patent application Ser. No. 63/017,782 filed on Apr. 30, 2020 the disclosure of which is incorporated herein in its entirety by reference.

TECHNICAL FIELD

This invention relates to dehydration of alcohols such as methanol and ethanol and an apparatus and method for doing so.

BACKGROUND

In many industrial, medical drug, and pharmacological processes using hydrophilic alcohols such as methanol or ethanol as a solvent, the alcohol absorbs moisture or water and becomes less effective and eventually must be either disposed of or dehydrated and reused. In processes for extracting so called essential oils or plant oil from oil bearing plant material which use ethanol as a solvent, its efficiency decreases if it has absorbed more than 5% of water by weight (less than 190 proof) and in some plant oil extraction processes it is desirable to use essentially pure or absolute ethanol (199 to 200 proof). Typically, in plant oil extraction processes an ethanol solvent becomes unusable or economically unfeasible after it absorbs about 10% to 20% of water (180 to 140 proof).

One prior art approach for dehydrating an ethanol/water mixture is fractional distillation usually in a batch process which requires heating the mixture which uses a lot of energy and significant manual intervention and observation. Another prior art approach is passing the mixture through beds of 3-A beads to remove the water which requires an inert gas purge so that the ethanol does not absorb moisture from the air and produces nearly 200 proof ethanol which is unstable in air and stabilizes at about 190 proof. This method is also labor intensive and requires a lot of energy to recharge the beads by heating them in a vacuum for an extended period of time.

Thus, there is a need for an ethanol dehydration process which is energy efficient, requires little to no operator intervention or time and if desired may be automated.

SUMMARY

In at least some implementations a method of dehydrating a hydrophilic solvent/water mixture such as an ethanol/water mixture may include pressurizing the mixture to at least 40 psig, heating the pressurized mixture to a temperature of at least 170° F., passing the heated and pressurized mixture through at least one Zeolite separator to produce separate streams of water and pressurized and heated dehydrated ethanol, and using the pressurized and heated dehydrated ethanol to at least in part heat the pressurized mixture and to cool the pressurized and heated dehydrated ethanol. In at least some implementations the process may include cooling the pressurized and heated dehydrated ethanol to a temperature below its boiling point at atmospheric pressure. In at least some implementations the process may include applying a vacuum to the water stream side of the Zeolite separator. In at least some implementations the process may include cooling the stream of water to a temperature of less than about 200° F.

At least some implementations of an apparatus for dehydrating an alcohol and water mixture may include a pump to pressurize a liquid alcohol and water mixture to a super-atmospheric pressure of at least 40 psig, a heat exchanger to heat the pressurized mixture to a temperature of at least about 170° F., a molecular membrane separator to separate water from the heated and pressurized mixture and to produce separate streams of water and pressurized dehydrated alcohol, and the separator connected with the heat exchanger to pass the stream of pressurized dehydrated alcohol through the heat exchanger to at least in part heat pressurized mixture in the heat exchanger and to cool the stream of pressurized dehydrated alcohol to a temperature lower than the temperature of its boiling point at atmospheric pressure.

In at least some implementations the apparatus may include a heater configured to maintain or heat the pressurized alcohol and water mixture in the membrane separator to a temperature of at least 190° F. At least some implementations may include a heat exchanger to cool the water from the membrane separator. At least some implementations may include a vacuum pump to produce a vacuum on the water side of the heat exchanger and/or on the water stream side of the membrane separator. At least some implementations may include a tank to receive cooled dehydrated alcohol and a pump configured to supply cooled dehydrated alcohol from the tank. Some implementations may include a heat exchanger configured to cool the water from the membrane separator.

At least some implementations of the apparatus may include heating the dehydrated alcohol from at least one of the heat exchanger or the membrane separator to a temperature of at least 225° F. to vaporize the dehydrated alcohol, passing the vaporized dehydrated alcohol through a sieve filter assembly of 3A beads to remove water vapor from the dehydrated alcohol to produce alcohol vapor of at least 199 proof. Some implementations of the apparatus may include a vacuum pump to provide a vacuum on the sieve filter assembly. Some implementations of the apparatus may include a condenser assembly to condense the alcohol vapor of at least 199 proof to liquid alcohol at atmospheric pressure.

BRIEF DESCRIPTION OF THE DRAWINGS

The following detailed description of certain embodiments and best mode will be set forth with reference to the accompanying drawings in which.

DETAILED DESCRIPTION OF THE PREFERRED EMBODIMENTS

In at least some implementations a method of dehydrating an alcohol/water mixture such as an ethanol mixture with more than 5% water by weight (herein after sometimes referred to an ethanol/water mixture, the mixture, or as less than 190 proof ethanol) may include the steps of maintaining the mixture at a super-atmospheric pressure and a temperature of about 190° F. and desirably about 230° to 250° F. while passing it through at least one Zeolite separator to remove water from the mixture and provide a water stream and a separate liquid stream of pressurized dehydrated ethanol, and to cool the dehydrated ethanol. In at least some applications, the super-atmospheric pressure of the mixture may be in the range of about 40 to 75 psig.

In at least some applications, the pressurized dehydrated ethanol may flow from the separator at a temperature of at least 190° F. and desirably about 230° to 250° F. and be passed through one side of a heat exchanger upstream of the separator to at least in part heat the mixture supplied to the separator and to cool the dehydrated ethanol to a temperature below its boiling point at atmospheric pressure. In at least some applications a heating medium is supplied to the separator to heat the mixture therein to a temperature of at least 200° F. and desirably about 230° to 250° F. In at least some applications, the heating medium supplied to the separator may be steam. In at least some applications a vacuum may be applied to the water side of the separator which is believed to increase the rate at which water is separated from the mixture to produce dehydrated ethanol.

In some applications of the method, the dehydrated ethanol from the separator may be heated to a vapor state and passed through a molecular sieve with 3A beads to remove water moisture from the dehydrated ethanol to provide essentially pure or absolute ethanol of about 199 to 200 proof. Periodically the 3A beads must be regenerated or water vapor removed from them such as by heating to a temperature of about 350° to 500° F. in a vacuum or an inert gas such as a nitrogen atmosphere for an extended period of time.

Figure 1:
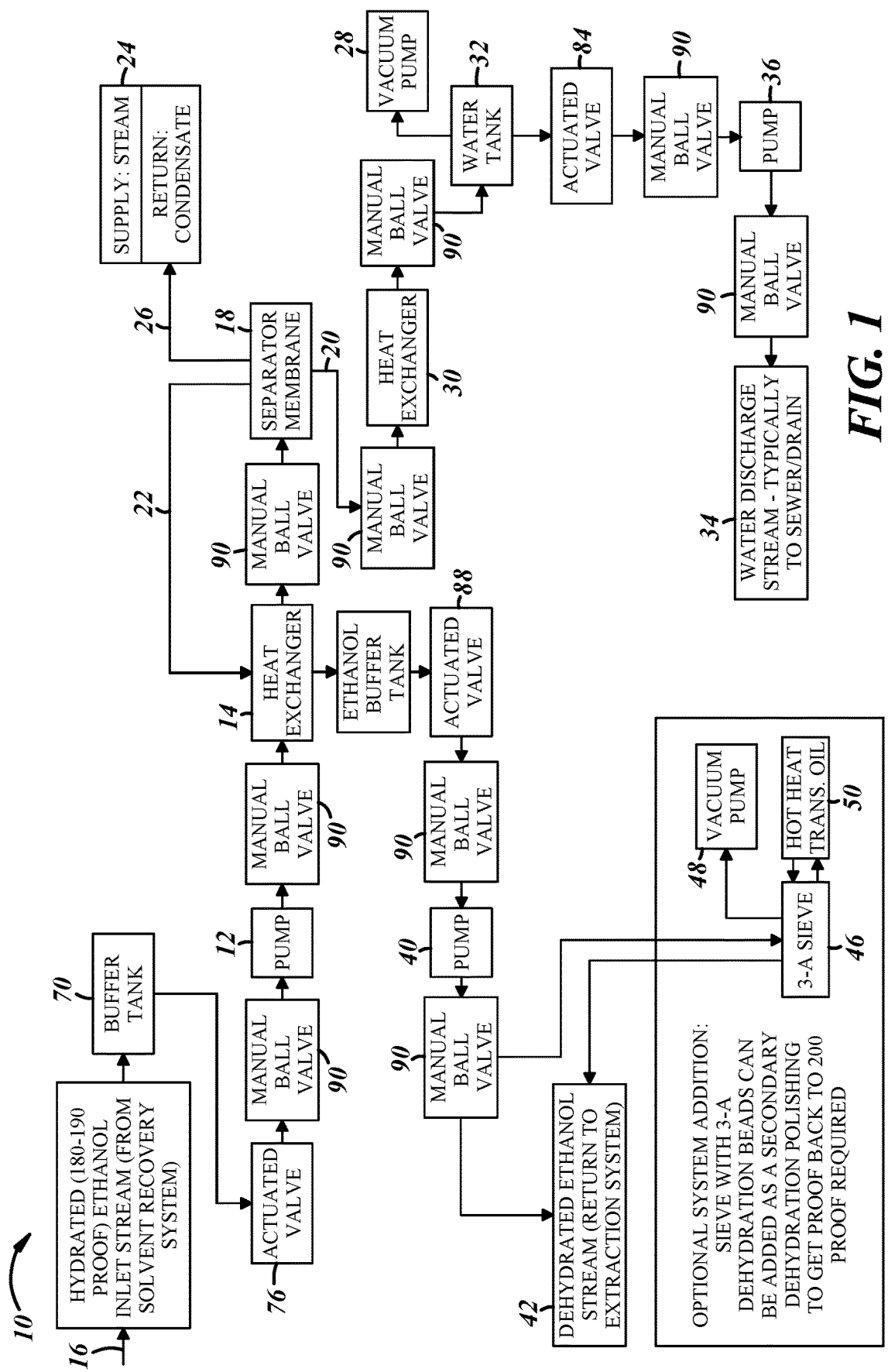
FIG. 1 is a schematic drawing of a hydrophilic alcohol dehydration apparatus.

As shown FIG. 1, in some applications an apparatus 10 for dehydrating an ethanol/water mixture, may include a pump 12 and a heat exchanger 14 which in operation may flow a liquid ethanol/water mixture 16 at a super-atmospheric pressure and a heated elevated temperature through a membrane separator assembly 18 to separate water 20 from the mixture and provide liquid dehydrated ethanol 22 which may be of at least about 189 proof, and may flow this dehydrated ethanol 22 through the heat exchanger 14 to at least in part heat the ethanol/water mixture 16 flowing to the membrane separator and to at least in part cool the dehydrated ethanol 22 which may be cooled to a temperature below its boiling point at atmospheric pressure.

In some applications, the pump may increase the pressure of the ethanol/water mixture 16 from substantially atmospheric pressure to a pressure which when heated maintains this mixture 16 in liquid form which pressure may be in the range of 40 to 75 psi, and the heat exchanger 14 may preheat the pressurized ethanol/water mixture 16 from substantially ambient temperature to a temperature usually of at least about 175° F. and desirably in the range of about 175° to 195° F.

In at least some applications, the temperature of the pressurized ethanol/water mixture flowing through the separator assembly 18 may be maintained at or increased to a temperature in the range of about 230° to 250° F. by a suitable heat source such as steam from a steam supply 24 to which condensate 26 from the separator assembly 18 may be returned. Of course skilled persons may readily devise other suitable sources and devices for maintaining the temperature of or further increasing the temperature of the ethanol/water mixture in the separator assembly.

In some applications, a vacuum may be applied to the water side of the membranes of the separator assembly such as by a vacuum pump 28 which is believed to increase the rate at which the separator assembly 18 separates water from or dehydrates the ethanol/water mixture 16.

In at least some applications, the apparatus 10 optionally may include a heat exchanger 30 which may condense and or cool the water vapor and water from the separator assembly 18 to a temperature of less than about 200° F. and desirably less than about 175° F. which if desired may then be sent to a holding tank 32. Periodically water from the holding tank may be typically discharged to a drain or sewer 34 or if required by governmental regulations to a treatment facility such as by a water pump 36.

In at least some applications, the dehydrated ethanol 22 may flow from the heat exchanger 14 to a buffer or holding tank 38 from which it may be intermittently transferred such as by a pump 40 to an extraction system 42 for reuse.

Optionally, if it is desired to remove more moisture from the dehydrated ethanol to produce absolute ethanol typically of 199 to 200 proof, dehydrated ethanol 22 from either the outlet side of the heat exchanger 14 or from the membrane separator 18 or both may be further processed by a secondary extraction system 44. The system 44 may include a molecular sieve assembly 46 with a bed of 3A beads through which the dehydrated ethanol is passed in vapor form such as by being heated to a temperature typically in the range of about 248° to 300° F. Desirably a vacuum may be applied by a pump 48 to the downstream side of the bed of 3A beads to increase the flow rate through the bed and decrease the temperature to which the dehydrated ethanol must be heated to vaporize it. The absolute ethanol vapor produced by the molecular sieve assembly may then be condensed to a liquid at atmospheric pressure and desirably atmospheric temperature and transferred to the extraction system for reuse. The sieve assembly may be heated by a suitable heat source such as a heater assembly 50 which circulates hot oil through a heat exchanger of the sieve assembly. Periodically the 3A beads must be recharged to remove the moisture from them so that they are suitable for reuse.

Figure 2:
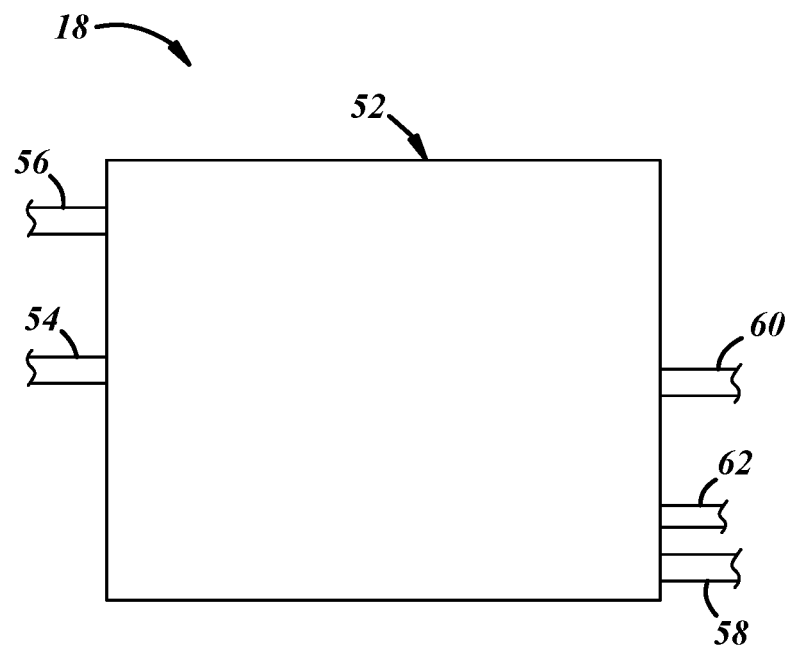
FIG. 2 is a side view of a membrane separator assembly of the apparatus of FIG. 1.
Figures 3, 4:
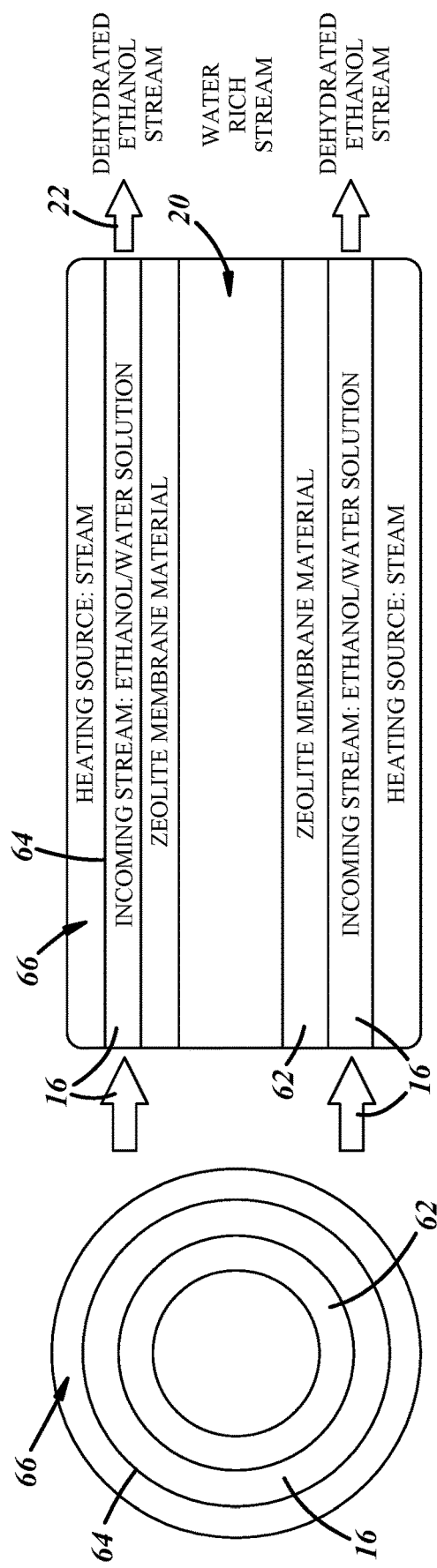
FIG. 3 is a schematic end view of a tubular membrane of the separator assembly of FIG. 2.
FIG. 4 is a schematic sectional view of the tubular membrane of FIG. 3.

As shown in FIG. 2, the membrane separator assembly 18 may include a vessel or housing 52 with an ethanol/water mixture inlet 54, a steam inlet 56, a steam condensate outlet 58, a water or water vapor outlet 60, and a dehydrated ethanol outlet 62. As shown in FIGS. 3 and 4, within the housing there may be at least one and typically a plurality of tubes 62 of a 4A zeolite membrane material the outer surface of which may be in contact with the incoming ethanol/water mixture 16 which also may be in contact with an imperforate annular inner wall 64 of a steam heating chamber 66 in thermal heat transfer relationship with the ethanol/water mixture. In operation the zeolite membrane separates the water or moisture from the mixture 16, and the water is discharged through the housing outlet 60 and the dehydrated ethanol is discharged through the housing outlet 62. Steam may enter the chamber 66 through the housing inlet 56 and condensate and or steam may be discharged from the chamber through the outlet 58. Desirably in the separator assembly 18 the ethanol/water mixture and the dehydrated ethanol are maintained at a high enough super-atmospheric pressure and a low enough elevated temperature so that they remain in liquid form. With sufficient pressure, this elevated temperature may be and typically is above the boiling point temperature of dehydrated ethanol at atmospheric pressure and sea level which is about 174° F.

Figure 5:
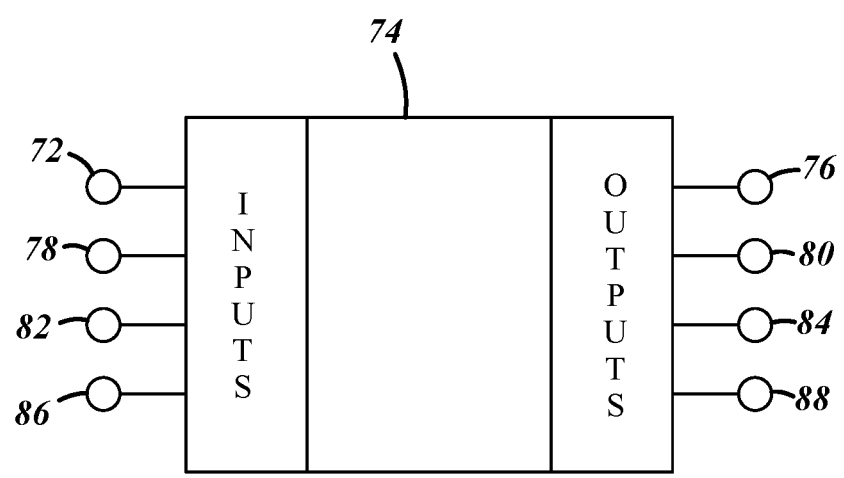
FIG. 5 is a sensor and control schematic of the apparatus of FIG. 1.

The apparatus 10 may be configured for substantially continuous operation which if desired may be automated. As shown in FIGS. 1 and 5, the apparatus may have a buffer tank 70 with an associated level sensor 72 providing a signal to an electronic controller such as a PLC 74 to control the filling of the buffer tank with an ethanol/water mixture 16 typically at ambient pressure and temperature and a solenoid actuated valve 76 to control the supply of the mixture to the pressurizing pump 12 which may be continuously operated so long as there is an adequate quantity or level of the mixture in this buffer tank. To control and maintain a desired temperature of the membrane separator assembly 18, a temperature sensor 78 associated with the membrane separator 18 may provide a signal to the PLC to control a solenoid actuated valve 80 to control the flow of steam to the separator assembly 18. The PLC may also control operation of the vacuum pump 28.

To control the discharge of water from the holding tank 32, a level sensor 82 associated with the holding tank may provide a high level or "full" signal to the PLC which may turn off the vacuum pump 28, open a solenoid actuated flow control valve 84 and energize the pump 36 to remove water from this tank, and when a low level of water in the tank is indicated by the sensor 82 the PLC may turn off the pump 36, close this flow control valve and turn on the vacuum pump 82. To control the level of dehydrated ethanol in the buffer tank 38, a level sensor 86 associated with this tank may provide a high level or "full" signal to the PLC which may then open a solenoid actuated valve 88 and energize the pump 40 to remove dehydrated ethanol from this buffer tank and when a low level of dehydrated ethanol is indicated by this sensor the PLC may turn off this pump and close this control valve.

If the optional further moisture removal system 44 is included, the PLC may also control the cycling of the vacuum pump 48 and the operating temperature of the sieve assembly 46 such as by using a signal from an associated temperature sensor to control a solenoid actuated valve controlling the flow rate of hot oil from the heater assembly 50 through the sieve assembly.

As shown in FIG. 1, to facilitate service, maintenance, repair and or replacement of various components of the apparatus 10, manual shutoff valves such as ball valves 90 may be included in the apparatus. In operation of the apparatus these shutoff valves are normally open.

The forms of the invention disclosed herein constitute presently preferred embodiments and many other forms and embodiments are possible and will occur to persons skilled in the art. It is not intended herein to mention all of the possible equivalent forms or ramifications of the invention. It is understood that the terms used herein are merely descriptive, rather than limiting, and that various changes can be made without departing from the spirit or scope of the invention which is particularly desirable for efficiently and economically dehydrating ethanol for reuse in plant oil extraction processes and apparatus or other processes and apparatus using hydrophilic alcohols which in use absorb water and water vapor.

The invention claimed is:

1. An apparatus for dehydrating an alcohol and water mixture comprising:
    a pump configured to pressurize a liquid alcohol and water mixture to a super-atmospheric pressure of at least 40 psig;
    a heat exchanger configured to heat the pressurized mixture to a temperature of at least about 170° F.;
    a molecular membrane separator configured to separate water from the pressurized and heated mixture and to produce separate streams of water and pressurized dehydrated alcohol; and
    the molecular membrane separator operably connected with the heat exchanger to pass the stream of pressurized dehydrated alcohol through the heat exchanger to at least in part heat pressurized mixture in the heat exchanger and to cool the stream of pressurized dehydrated alcohol to a temperature lower than the temperature of its boiling point at atmospheric pressure, further comprising heating the dehydrated alcohol from at least one of the heat exchanger or the molecular membrane separator to a temperature of at least 225° F. to vaporize the dehydrated alcohol, passing the vaporized dehydrated alcohol through a sieve filter assembly of 3A beads configured to remove water vapor from the dehydrated alcohol to produce alcohol vapor of at least 199 proof.

2. The apparatus of claim 1 which also comprises a heater configured to maintain or heat the pressurized alcohol and water mixture in the membrane separator to a temperature of at least 190° F.

3. The apparatus of claim 1 which also comprises a tank configured to receive cooled dehydrated alcohol and a pump configured to supply cooled denatured alcohol from the tank.

4. The apparatus of claim 1 which also comprises a vacuum pump configured to produce a vacuum on the water stream side of the molecular membrane separator.

5. The apparatus of claim 1 which also comprises a heat exchanger configured to cool the water from the molecular membrane separator.

6. The apparatus of claim 5 which also comprises a vacuum pump configured to produce a vacuum on the water side of the heat exchanger and on the water stream side of the molecular membrane separator.

7. The apparatus of claim 1 which also comprises a heat exchanger configured to cool the stream of water from the molecular membrane separator to a temperature of less than 175° F.

8. The apparatus of claim 1 which also comprises a heat exchanger to cool the water from the molecular membrane separator and a tank configured to receive the cooled water from the heat exchanger.

9. The apparatus of claim 8 which also comprised a pump configured to supply cooled water from the tank.

10. The apparatus of claim 1 which also comprises a vacuum pump configured to provide a vacuum for the sieve filter assembly.

11. The apparatus of claim 1 which also comprises a condenser assembly configured to condense the alcohol vapor of at least 199 proof to be liquid alcohol at atmospheric pressure.

12. The apparatus of claim 11 which also comprises a vacuum pump configured to provide a vacuum for the sieve filter assembly.

13. The apparatus of claim 1 wherein the sieve filter assembly comprises a plurality of 3A beads.

14. The apparatus of claim 1 wherein the alcohol/water mixture comprises an ethanol/water mixture.

15. A method of dehydrating an ethanol/water mixture comprising;
    pressurizing an ethanol/water mixture to a pressure of at least 40 psig;
    heating the pressurized mixture to a temperature of at least 170° F.;

passing the pressurized and heated mixture through at least one Zeolite separator to produce separate streams of water and pressurized and heated dehydrated ethanol;

using the pressurized and heated dehydrated ethanol to at least in part heat pressurized mixture and to cool the pressurized and heated dehydrated ethanol;

heating the dehydrated ethanol to a temperature of at least 225° F. to vaporize the dehydrated ethanol; and passing the vaporized dehydrated ethanol through a sieve filter assembly of 3A beads configured to remove water vapor from the dehydrated ethanol to produce ethanol vapor of at least 199 proof.

16. The method of claim 15 in which the step of using the pressurized and heated dehydrated ethanol to at least in part heat the pressurized mixture includes cooling the pressurized and heated dehydrated ethanol to a temperature below its boiling point at atmospheric pressure.

17. The method of claim 15 which also comprises applying a vacuum to the water stream side of the Zeolite separator.

18. The method of claim 15 which also comprises cooling the stream of water to a temperature of less than about 200° F.

19. The method of claim 15 which also comprises putting the cooled dehydrated ethanol in a tank and intermittently removing at least part thereof from the tank.

\* \* \* \* \*